United States Patent
O'Connor

(12) 
(10) Patent No.: US 7,095,410 B2
(45) Date of Patent: Aug. 22, 2006

(54) METHOD FOR GENERATING AND DISPLAYING COMPLEX DATA UTILIZING COLOR-CODED SIGNALS

(76) Inventor: Henry Moncrieff O'Connor, 201 Horace Ave., Virginia Beach, VA (US) 23462

( * ) Notice: Subject to any disclaimer, the term of this patent is extended or adjusted under 35 U.S.C. 154(b) by 654 days.

(21) Appl. No.: 09/740,042

(22) Filed: Dec. 20, 2000

(65) Prior Publication Data

US 2001/0052905 A1 Dec. 20, 2001

Related U.S. Application Data

(60) Provisional application No. 60/172,579, filed on Dec. 20, 1999.

(51) Int. Cl.
*G06T 11/20* (2006.01)

(52) U.S. Cl. ............................................. 345/440
(58) Field of Classification Search .......... 345/440.1, 345/440; 324/76.12, 348, 522
See application file for complete search history.

(56) References Cited

U.S. PATENT DOCUMENTS

| | | | |
|---|---|---|---|
| 3,952,315 A | 4/1976 | Cecco et al. | |
| 4,058,826 A | * 11/1977 | Schneider | ............... 358/10 |
| 4,140,997 A | 2/1979 | Brady | |
| 4,362,973 A | 12/1982 | Brentlinger | |
| 4,424,486 A | 1/1984 | Denton et al. | |
| 4,586,249 A | 5/1986 | Costlow et al. | |
| 4,608,534 A | 8/1986 | Cecco et al. | |
| 4,630,229 A | 12/1986 | D'Hondt | |
| 4,631,533 A | * 12/1986 | Mark, Jr. | ............... 340/721 |
| 4,644,336 A | 2/1987 | Mark, Jr. | |
| 4,646,013 A | 2/1987 | Tornblom | |
| 4,648,113 A | 3/1987 | Horn et al. | |
| 4,763,274 A | 8/1988 | Junker et al. | |
| 4,768,086 A | 8/1988 | Paist | |
| 4,808,924 A | 2/1989 | Cecco et al. | |
| 4,808,927 A | 2/1989 | Cecco et al. | |
| 4,851,774 A | 7/1989 | Tornblom | |
| 4,855,676 A | 8/1989 | Cecco et al. | |
| 4,965,519 A | 10/1990 | Tornblom | |
| 4,977,514 A | * 12/1990 | Bush | ............... 364/487 |
| 5,017,869 A | 5/1991 | Oliver | |
| 5,019,777 A | 5/1991 | Gulliver et al. | |
| 5,049,817 A | 9/1991 | Cecco et al. | |
| 5,166,779 A | 11/1992 | Moyer | |
| 5,182,513 A | 1/1993 | Young et al. | |
| 5,235,413 A | 8/1993 | Knierim | |
| 5,237,270 A | 8/1993 | Cecco et al. | |
| 5,241,473 A | 8/1993 | Ishihara et al. | |
| 5,298,996 A | 3/1994 | Stelling | |
| 5,383,114 A | * 1/1995 | Chambers | ............... 702/16 |
| 5,444,733 A | 8/1995 | Coassin et al. | |
| 5,453,688 A | 9/1995 | Cecco et al. | |
| 5,483,160 A | 1/1996 | Gulliver et al. | |
| 5,506,503 A | 4/1996 | Cecco et al. | |
| 5,533,510 A | 7/1996 | Koch, III et al. | |
| 5,539,303 A | 7/1996 | Okazako et al. | |
| 5,789,913 A | 8/1998 | Mager | |
| 5,793,205 A | 8/1998 | Griffith et al. | |
| 5,797,843 A | 8/1998 | Fitch et al. | |
| 5,883,298 A | 3/1999 | Holzapfel et al. | |
| 5,889,513 A | 3/1999 | Yeh | |
| 5,969,275 A | 10/1999 | Moe | |
| 5,973,620 A | 10/1999 | Holzapfel et al. | |

OTHER PUBLICATIONS

Derwent 2003–608645, 2004.*

* cited by examiner

*Primary Examiner*—Mark Zimmerman
*Assistant Examiner*—Scott Wallace
(74) *Attorney, Agent, or Firm*—Millen, White, Zelano & Branigan, P.C.

(57) ABSTRACT

Color coded signals are superimposed upon one another in order to more conveniently understand phenomenon to which the signals relate. A specific application of the technique is non-destructive eddy-current testing of tubes used in devises such as nuclear reactors for detecting anomalies such as pits, through-holes and dents. The signals generated during the eddy tests are displayed as overlapping lissajous transforms which produce distinctive color patterns for each anomaly.

17 Claims, 11 Drawing Sheets

  
FIG. 10a     FIG. 10b     FIG. 10c
 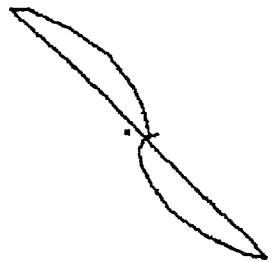 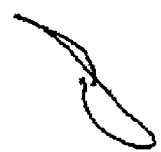
FIG. 11a     FIG. 11b     FIG. 11c
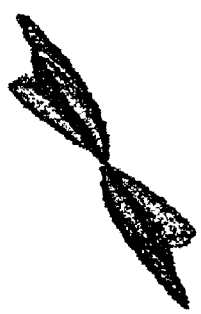 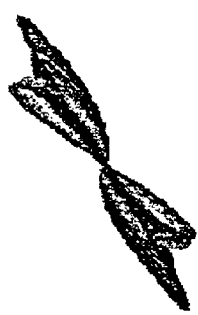  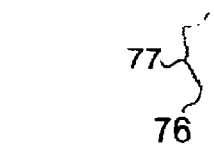
FIG. 12a     FIG. 12b     FIG. 12c

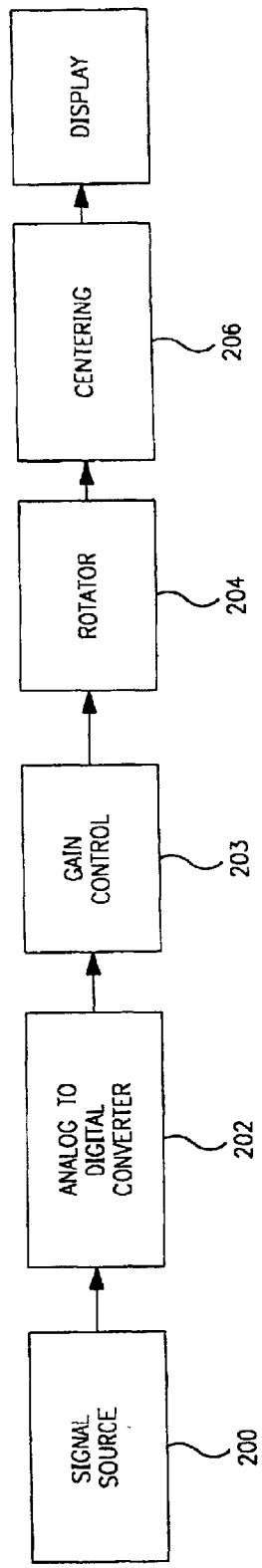
FIG. 16
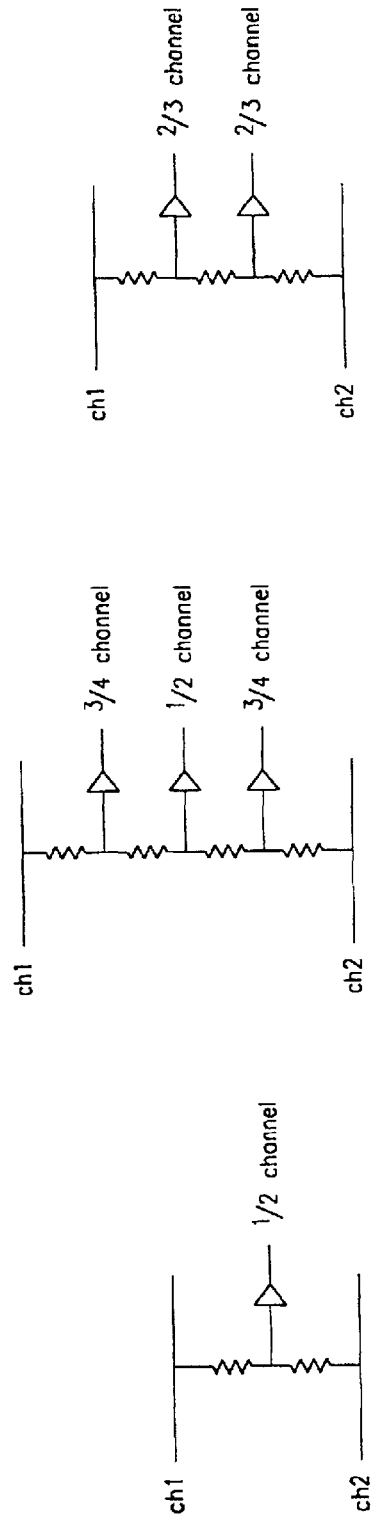
FIG. 17a
FIG. 17b
FIG. 17c

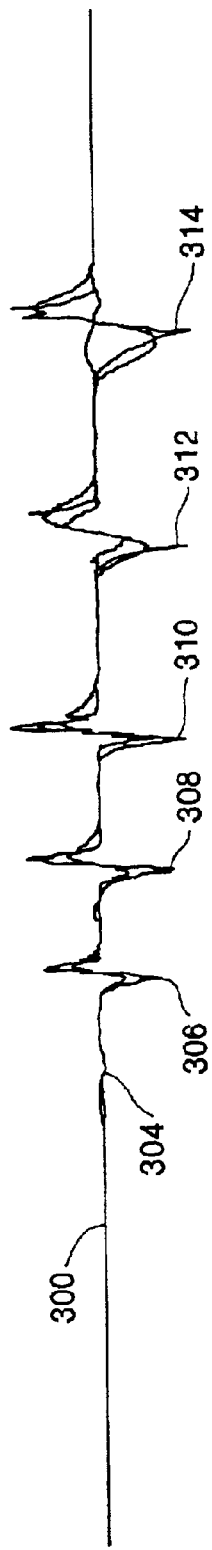
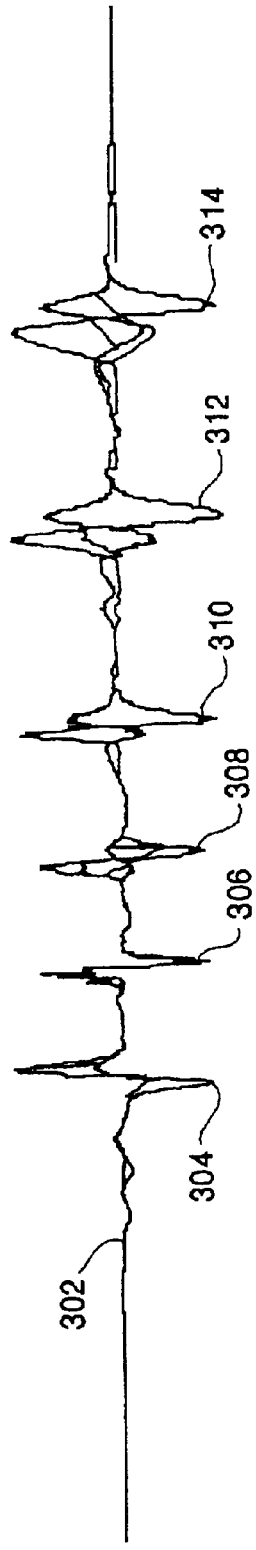
FIG. 18a
FIG. 18b

METHOD FOR GENERATING AND DISPLAYING COMPLEX DATA UTILIZING COLOR-CODED SIGNALS

RELATED APPLICATION

This application claims priority form U.S. Provisional Application Ser. No. 60/172,579 filed Dec. 20, 1999.

FIELD OF THE INVENTION

The present invention is directed to methods for generating and displaying complex data utilizing color-coded signals. More particularly, the present invention is directed to such methods wherein multiple signals, each having different variances, are displayed together in order to more conveniently and easily understand phenomenon to which the signals relate.

BACKGROUND OF THE INVENTION

When analyzing signals, it is often important to compare signals one to another visually in order to detect meaningful differences. Since these differences are frequently subtle, it is at times difficult for technical workers as well as highly trained professionals, e.g., engineers, scientists, physicians, seismologists, economists, etc. to both learn the meanings of and properly interpret displays of data that they are considering. Exemplary of such situations are the multiple, time variance signals encountered in displays such as displays for non-destructive, eddy current testing; non-destructive ultrasound testing and acoustic emission testing; multiple trace EKG displays and displays for seismology, sonar and electro-encephalography (EEG).

Exemplary of an undertaking in which it is difficult to analyze signals without considerable know-how and experience is non-destructive, eddy current testing of objects such as tubes or plates. In eddy current testing, the impedance of an eddy current probe actually changes with the probe's position in a tube or position over a test object; therefore, an eddy current signal is actually a signal that varies with position. By moving the probe through a tube, over a tube or over a test object, this spatially variant signal becomes a time variant signal. Even experienced inspectors can easily make mistakes because displays of test signals are not necessarily clear enough for an inspector to analyze signals.

When inspecting tubes, such as the heat exchange tubes used in power plants, it is time consuming and frequently difficult for even experienced eddy current inspectors to distinguish between signal wave forms representing roll stops, through-wall holes, pits, and magnetic inclusions. Roll stops introduced during fabrication and magnetic inclusions are generally considered harmless, whereas throughwall holes and relatively deep pits are hazards. In prior art approaches, magnetic inclusions and pits produce substantially similar signals in which only an inspector's considerable experience can be trusted in making a decision as to whether or not a hazard exists in a length of tubing to the extent that the length of tubing should be replaced or removed from service by plugging both ends with a resulting loss of efficiency. Replacement of a length of tubing is a time-consuming, relatively expensive undertaking which should, of course, be avoided wherever possible. However, if the heat exchanger is used with a nuclear reactor then chances cannot be taken and therefore many tubes which may be sound are replaced or removed from service upon detection of an anomaly which it is suspected of being pit, but is merely a harmless magnetic inclusion (a magnetic inclusion is the occurrence of an iron particle or other magnetic alloy particle in the wall of a tube).

Generally, these signals are displayed as "figure 8" signals, known as lissajous figures. Lissajous figures are generated by an endpoint of a vector which represents an unbalanced voltage or impedance of a bridge and therefore, variations in voltage or impedance of detector windings of a probe. When a defect appears, a "figure 8" display occurs, with the peak-to-peak amplitude of the "figure 8" determining the volume of the defect and the phase corresponding to the depth of the defect. One way to recognize and differentiate between these defects is to apply signals of different frequencies. Typically, four frequencies are used and the resulting signals are displayed on four separate portions of a computer screen to the test object so that they may be visually compared. Visually comparing the signals in four separate sections of a screen is at times difficult so there is needed an approach in which the "figure 8" signals are visually displayed so that differences which relate to anomalies may be more readily detected and understood. That there is a difficulty involved in interpreting these signals is set forth in U.S. Pat. No. 4,763,274 issued Aug. 9, 1988, having the title "Machine Implemented Analysis Eddy Current Data", incorporated herein in its entirety by reference. In an effort to make these signals easier to interpret, color displays have been used for strip charts as set forth in U.S. Pat. No. 4,644,336 issued Feb. 17, 1987 and titled "Color Display of Related Parameters", incorporated herein in its entirety by reference. Color displays have also been used with lissajous figures as set forth in U.S. Pat. No. 4,631,533 issued Dec. 23, 1986 and titled "Display of Eddy Current Detector Data", incorporated herein in its entirety by reference. These displays do not improve visual representation to an extent sufficient to reduce chances of error by either experienced or inexperienced tube inspectors, but serve only to indicate which signal on the screen pertains to a specific frequency channel. This can also be accomplished without the use of color by placing each eddy current signal at a different location on one screen and having some means to label each section of the screen to indicate the frequency channel.

Improving visual representation is a concern with other signals which are indicative of many different phenomenon. Exemplary of such are the frequency signals displayed for EKGs, seismology, sonar, EECs, music, other audible signals, and an entire host of situations where anomalies are uncovered by a comparative analysis.

SUMMARY OF THE INVENTION

The present invention is directed to methods for displaying signals obtained from monitoring phenomenon in order to indicate the occurrence of an anomaly in the phenomenon. The invention comprises producing, while the phenomenon is being monitored, multiple real signals in electronic form, the multiple real signals each having a standard characteristic and real parameters of different real values. The multiple real signals are interpolated to provide multiple virtual signals having the standard characteristic of the multiple real signals and virtual parameters between the real parameters. A separate color is assigned to each of the multiple signals to produce multiple color-coded signals; which color-coded signals are displayed while superimposed on one another (rather than on separate portions of a screen as in prior art) to indicate that an anomaly has occurred in the phenomenon.

In a further implementation of the invention, the real signals are analog signals, and the real analog signals are interpolated to produce the multiple virtual signals.

In a further aspect of the invention, the analog virtual signals and the analog real signals are digitalized before displaying the signals in separate colors.

In a further aspect of the invention, the characteristic signals may have a different DC offset; therefore, the signals are centered by bringing the signals to a standard baseline by adjusting the real values of the real signals.

In one embodiment of the invention, the phenomenon is an eddy current, induced in a metallic object and the anomaly is a defect in the metallic object. The metallic object may be a tube, the anomaly being a defect in the tube.

In a more specific aspect of the invention, the multiple real signals are produced with a differential probe, and the multiple real and virtual signals are converted to lissajous waveforms generated by voltage vector sweeps and phase angles when the multiple signals are displayed. When the phenomenon being investigated is an eddy current or eddy currents in the wall of a tube, the anomaly is one occurring in a group of anomalies comprising through holes, interior pits, exterior pits, magnetic inclusions, dents and roll stops, each of which has a corresponding distinctive display of multiple color-coded signals.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts through the several views, and wherein:

FIGS. 10a–10c are frequency channel transforms showing occurrence an interior diameter pit in a tube;

FIGS. 11a–11c are prior art lissajous figures illustrating a magnetic inclusion, hole and a roll stop, occurring in a tube;

FIGS. 12a–12c are frequency transforms illustrating a detection of a magnetic inclusion;

FIG. 15a is a diagrammatical illustration of a display screen a computer, a probe and a key pad useful for practicing the method of the present invention; while FIG. 15b shows various waveforms and transforms which occur on the computer screen of FIG. 15a;

FIG. 16 is a block diagram illustrating the steps employed in practicing a method of the present invention;

FIGS. 17a–17c are divider networks used to create virtual signals; and

FIGS. 18a and 18b are frequency signals specifically for eddy current testing but illustrative of other types of frequency signals.

DETAILED DESCRIPTION

Figure 1:
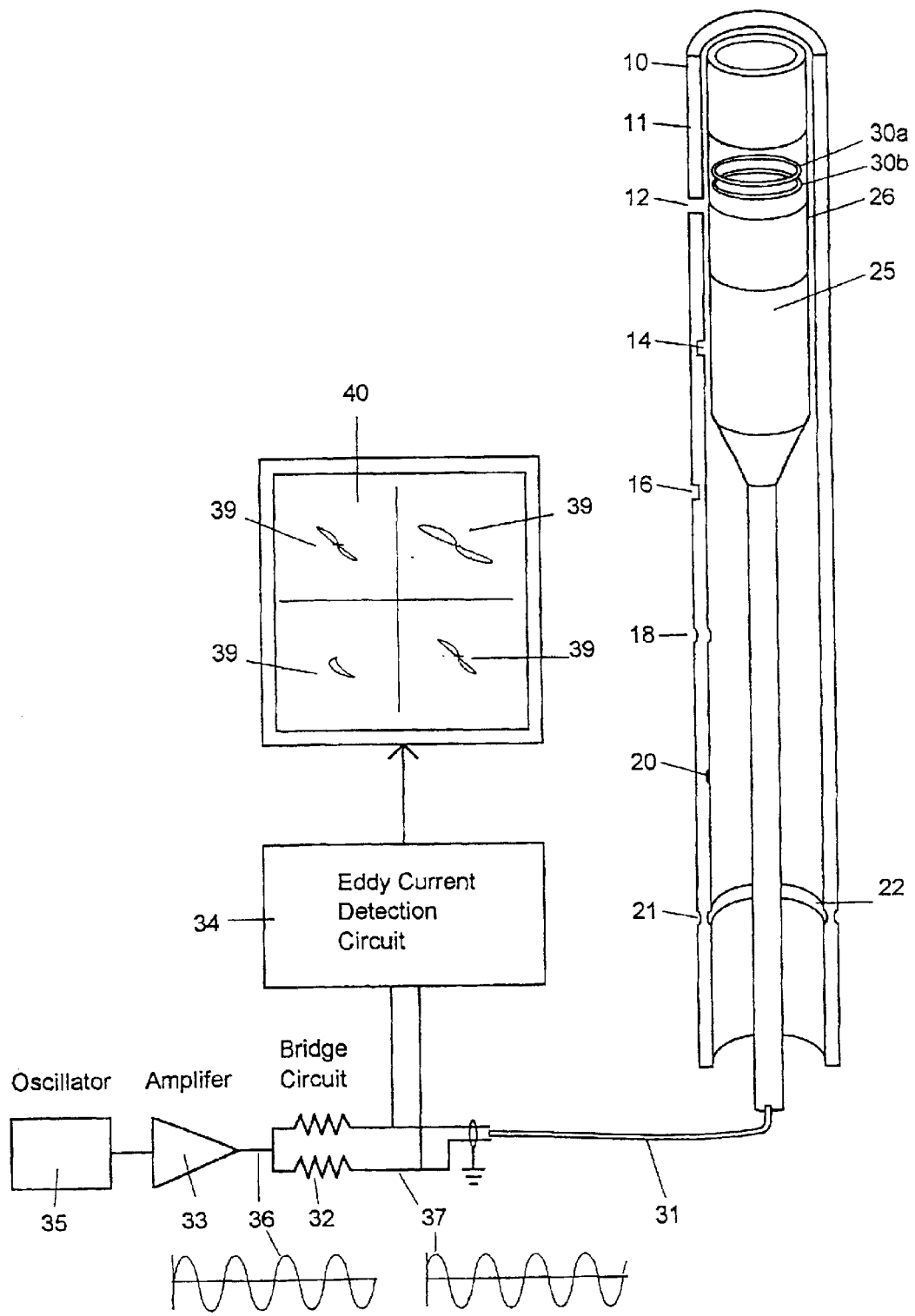
FIG. 1 is a block diagram showing a general prior art eddy current testing instrument arrangement over which the present invention is used.

Referring now to FIG. 1, there is shown the most common prior art arrangement for testing a non-ferrous alloy tube 10 to detect in the wall 11 thereof anomalies such as through-holes 12, interior pits 14, exterior pits 16 and dents 18. Also illustrated is a magnetic inclusion or deposit 20 and an outside circular groove 21 superimposed on an inside circular groove 22 indicative of an anomaly formed by a roll stop. These last two anomalies are, in almost all instances, harmless. Differentiating of these anomalies and of harmful defects is of utmost importance in ensuring the integrity of non-ferrous alloy tubes 10, which may be used, for example, as the heat exchanger tubes in nuclear power plants.

A typical arrangement for detecting the presence of the anomalies 12–22 in a non-ferrous tube 10 utilizes a probe 25. The probe 25 is a cylindrical device comprising a cylindrical housing 26 having therein, in the case of a differential detector, receiving coils 30a and 30b. As the probe 25 is advanced through the tube 10 with the coils 30a and 30b generating eddy currents in the wall of the tube 11, the coils 30a and 30b detect the voltage and phase of the eddy current fields induced in the wall 11 of the tube 10. If only absolute values are to be detected only one of the receiving coils 30a and 30b is monitored.

A cable 32 connects the probe 25 to an eddy current testing circuit 34 which includes an oscillator 35 which connected via the cable 32 to the coils 30a and 30b apply sine wave (or other wave shape) signals 36 to the coils. The coils 30a and 30b detect the voltage and phase of the eddy current in the wall 11 of the tube 10 and transmits via the cable 32 the voltage and phase of the eddy current in the form of an analog sinusoidal signal 37 to an eddy current detection circuit 38. Basically, the eddy current detection circuit 38 converts the sinusoidal signals 37 to Fourier waveforms 39 which are displayed on a display 40. In current day eddy current instruments, it is more common that two or more oscillators (often four) generate two or more simultaneous sine (or other wave shape) waves, which are applied simultaneously to the coils. The coils 30a and 30b detect the voltage and phase of all of these signals, and the eddy current detection circuit 38 convert each original signal into two time variant signals, which are each displayed as lissajous wave forms. Another form of the multi-frequency eddy current instruments emulates multiple, simultaneous sine (or other shape wave) form by rapidly switching the frequency of an oscillator in time. This is referred to as a multi-frequency eddy current instrument that uses time domain multiplexing. The display 40 is either a cathode ray tube or, preferably the monitor of a computer which has the display capabilities of a cathode ray tube.

Figure 2:
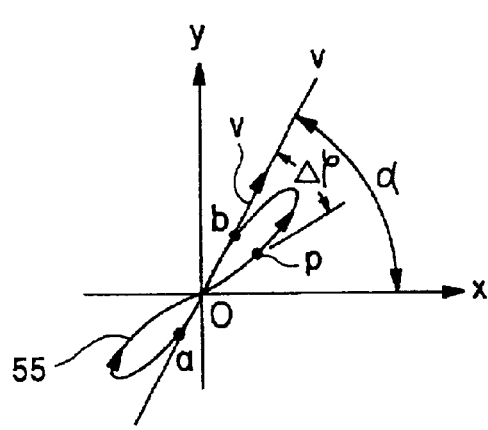
FIGS. 2, 3 and 4 are prior art diagrams illustrating a phase analysis of a differential defect signal derived from a prior art non-destructive, eddy current testing instrument such as that of FIG. 1.
Figure 3:
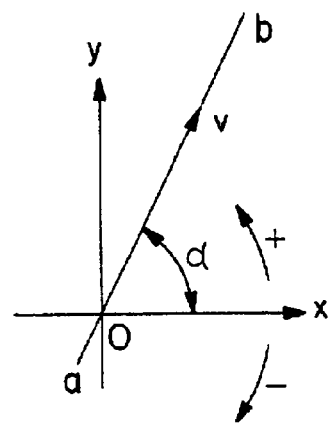
Figure 4:
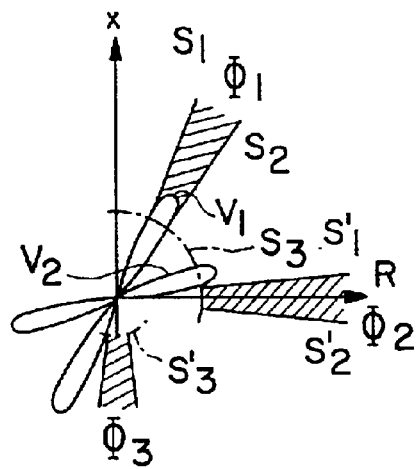

Referring now to prior art FIGS. 2–4, there is shown how "figure 8" lissajous waveforms are derived and how the waveforms illustrate the occurrence of a defect. In non-destructive eddy current testing, it is possible to determine scanning frequencies which permit selection of the phase separation of defect signals. A specific phase for one signal is set with a phase control. For example, a signal from a dent is set to be horizontal. Studying phase displacement between the current which passes through the coils 30a and 30b in the probe and a variation in unbalanced voltage of a bridge which results from variations in impedance of one of the two coils reveals the nature of the anomaly 12–22 detected.

In FIG. 2, the defect signal is represented by a moving point P corresponding to the end point of a vector V which represents the unbalanced voltage of the bridge formed by coils 30a and 30b and therefore corresponds to variations in impedance in these detector coils. The resulting trace 55 is a "figure 8" waveform. The defect modifies successively the impedance of the two windings 30a and 30b and causes two successive unbalances of the measuring bridge to create the "figure 8" display. The phase α of the "figure 8" varies depending upon the anomaly θ. When there is no anomaly such as the anomaly caused by the structural discontinuities 12–22, the "figure 8" signal does not occur because the end point P of the vector V remains at the center of the x-y coordinates.

As shown in FIG. 3, the detection of anomaly is represented by the vector V which originates at the center 0 of the "figure 8". The peak amplitude of the vector V is demonstrated by the peak-to-peak amplitude of the "figure 8" signal of FIG. 2. In eddy current testing the phase of the vector located above the 0-x axis is considered as being negative, and the phase of the vector being positive when it is located beneath the 0-x axis. The angle α of inclination the "figure 8" of FIG. 2 determines the nature of the anomaly and while the peak-to-peak amplitude of the "figure 8" signal determines its magnitude.

As is seen in FIG. 3, where a general demonstration of the principles underlying the present invention is shown, sector $\phi_1$ corresponds to localized defects local formation type; sector $\phi_2$ corresponds to external defects, and sector $\phi_3$ corresponds to internal defects. The magnitude of defects $\phi_1$, $\phi_2$, and $\phi_3$ and is determined by the peak-to-peak amplitude of "figure 8" waveforms written by the vector V.

Referring now to FIGS. 5a–5y, in accordance with the present invention there are twenty-five color-coded waveforms comprised of lissajous figures similar to those of FIG. 4, each of a different color and each representing a different frequency channel. Generally, the differential waveforms of FIGS. 5a–5y are frequency transforms created from frequency signals picked up by the coils 30a and 30b.

Figure 5:
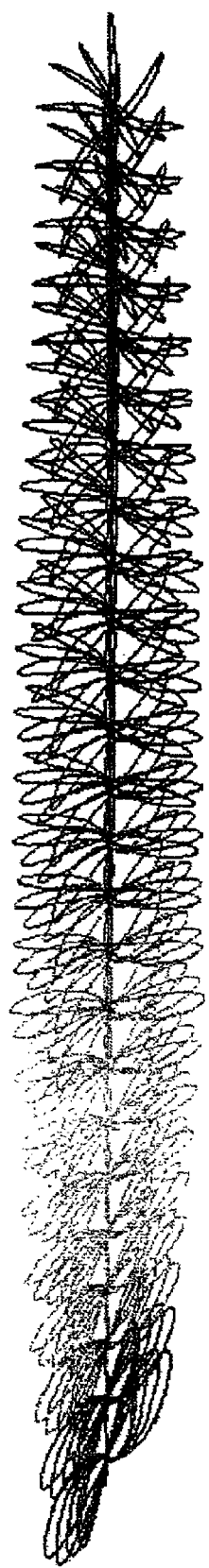
FIGS. 5a–5y are displays of differential frequency channels displayed as "figure 8" waveforms of various frequency channels with each frequency channel being color-coded a different color.
Figure 6:
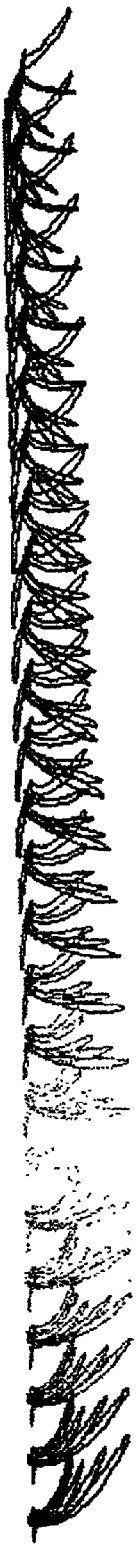
FIGS. 6a–6y are displays of waveforms of absolute signals of various frequency channel with each frequency channel being color-coded with a different color.

FIGS. 6a–6y illustrate color-coded absolute waveforms representing absolute values detected by a single coil 30a or 30b of probe 25 as opposed to the differential waveforms of FIG. 5. As with the waveforms of FIGS. 5a–5y, the waveforms rotate as frequency increases. Thus, for the anomalies shown, the phase angle α increases as the frequency increases. The FIGS. 5a–5y and 6a–6y signals are actually from a standard ASME Calibration Tube 10 with a dent 18 added to the list of ASME defects. In the ASME Calibration Tube 10, the shallower the pit 16, the larger the diameter of the pit; hence, the amplitude V of these signals are roughly the same. The signals of FIGS. 5a–5y are perhaps best understood in conjunction with FIGS. 8a–8c which are superimposed frequency channel transforms for a dent 18; FIGS. 9a–9c which are superimposed frequency channel transforms for a through hole 12, and FIGS. 7a–7c which are superimposed frequency channel transforms for outside diameter pits 16. In this regard, the generally horizontal signals 60 indicate a dent 18; the signals 61 occurring at approximately 45° in FIGS. 5e–5m indicate a through hole 12, and the signals 62, 63, 64 and 65 represent 80%, 60%, 40% and 20% outside diameter pits, respectively.

Preferably, as the frequency of the channel increases, so does the frequency of the color code. Accordingly, if the operator is familiar with the fact that the color of light changes as its frequency increases, there is an association between the increase in frequency of the frequency channels and the increase in the frequency of the light selected to correspond with that frequency channels.

| FIGS. | Frequency in Khz | Color |
| --- | --- | --- |
| FIGS. 5a–5c | 11–13 | red |
| FIGS. 5d–5g | 14–17 | orange |
| FIG. 5g | 19 | yellow |
| FIGS. 5h–5k | 20–26 | yellow green |
| FIGS. 5i–5m | 26–31 | green |
| FIGS. 5n–5o | 34–37 | blue-green |
| FIGS. 5p–5r | 40–48 | blue |
| FIGS. 5s–5t | 52–57 | blue-violet |
| FIGS. 5u–5w | 62–74 | violet |
| FIGS. 5x–5y | 81–88 | magenta |

As can be seen, the frequency ranges from low frequency red to high frequency violet with the highest frequency of FIG. 5y being magenta to mark the end frequency channel so that the frequency channel arrays are bracketed with similar colors.

Figures 7A, 7B, 7C:
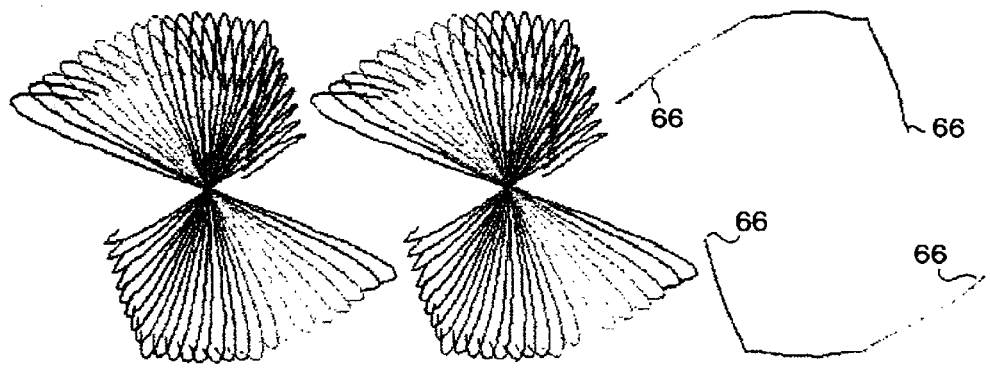
FIGS. 7a–7c are views showing the color-coded frequency transforms resulting when the waveforms of FIG. 5 are superimposed upon one another in a low to high arrangement in FIG. 7a, a high to low arrangement in FIG. 7b, and in a transform illustrating only end points in FIG. 7c; the illustrated waveform displaying detection of an outside diameter pit.

FIGS. 7a–7c illustrate a way to display multi-time variant signals as transforms. In FIGS. 7a–7c, the waveforms of FIGS. 5a–5y which are from detecting a 40% outside diameter pit 16 are superimposed upon one another so that the viewer has only the single lissajous transforms to study. FIGS. 7a and 7b show full lissajous transforms while FIG. 7c illustrates transform in which only the signal endpoints 66, representing the amplitude and phase of the waveforms of FIGS. 7a and 7b, have been connected while the lissajous waveforms have been deleted. In the FIG. 7a transform, the low frequency signal, i.e., the red signal of FIG. 5a has been drawn first and the high frequency signals, i.e., the violet signal of FIG. 5v and the magenta signal of FIG. 5y, have been drawn last. The intermediate frequencies represented by the orange through the blue waveforms of FIGS. 5p–5r have been drawn sequentially on the red waveform of FIGS. 5a–5c with the lower intermediate frequencies being drawn first. In the waveform of FIG. 7b, the frequencies have been drawn in the opposite order from the high frequency, i.e., magenta and violet, to the low frequency, i.e., red in descending order from FIG. 5y back to FIG. 5a. The display of FIGS. 7a–7c represents a 40% of wall outside diameter pit, such as the pit 16 shown in the tube 10 of FIG. 1.

Figures 8A, 8B, 8C:
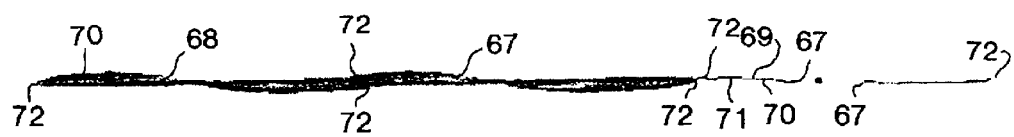
FIGS. 8a–8c are frequency channel transforms indicating the occurrence of a dent in a tube.
Figures 9A, 9B, 9C:
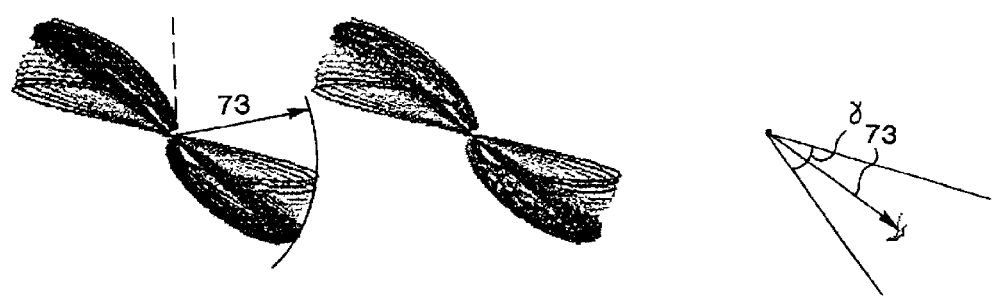
FIGS. 9a–9c are frequency channel transforms indicating the occurrence of a through hole in a tube.

Referring now to FIGS. 8a–8c, the transforms of a "dent signal" from a detent such as the dent 18 of FIG. 1 are shown. This is a very distinctive pattern because all of the lissajous figures are substantially horizontal. As is seen in FIG. 8c, as the frequency increases, the amplitude of the signal increases. Note that red signal 67 has relatively small amplitude, with the yellow, green, blue and violet signals 68–71, respectively, having increasingly larger amplitudes. Further note at the endpoints, that the magenta signal 72 representing the highest frequency of 88 Khz has the largest amplitude. This is clear from the high to low transform of FIG. 8b which the red signal 67 is shown having the smallest amplitude with the magenta signal 72 having the largest amplitude. In the low to high transform of FIG. 8a the red signal 67 has been overwritten so that this increase is not apparent. Since 88 Khz is the furthest from 11 Khz, a red transform 67 can be used with a magenta transform 72 without confusion. It is clear that the transforms of FIGS. 8a–8c from a dent signal, indicative of the dent 18 shown in the tube 10 of FIG. 1, are substantially different from the transforms of FIGS. 7a–7c, which represent the outside diameter pit 16 shown in FIG. 1. External anomalies in the tube 10 may be examined to determine if the exterior pit 16 or dent 18 is sufficiently serious to warrant replacement of the tube. If the tube 10 is not replaced or removed from service by plugging the ends, then the occurrence of exterior anomalies such as the exterior pit 16 or dent 18 can be logged for future reference and inspection.

Referring now to FIGS. 9a–9c, where transforms for a through hole 12 (FIG. 1) are shown, it is seen that the amplitude 73 of the signal remains substantially constant over the frequency range. However, the phase angle α rotates clockwise from the lowest frequencies to a maximum value in the mid-frequencies represented by the green and blue signals. The angle α then rotates counter-clockwise with the highest signal being the magenta signal of 88 Khz. It is clear that for a through-hole 12, as illustrated by the transforms of FIGS. 9a–9c, the waveforms are substantially different from the transforms of FIGS. 7a–7c for the outside diameter pit 16 and the transforms of FIGS. 8a–8c for the dent 18.

The eddy current instrument has been adjusted so that the signal from the dent 18 appears horizontal in all frequency channels using the phase control, which allows the signals to be rotated on the screen. Further the signal from the through-hole 12 has been adjusted in all channels to be the same amplitude. In this case, the dent 18 is considered to be the angle reference and the through-hole 12 is considered to be the magnitude reference. Other anomalies could have been chosen for the phase and amplitude reference, or the phase and amplitude reference could be the same anomaly. An equally successful result would be expected regardless of which anomaly is chosen as the phase reference and which is chosen as the amplitude reference.

Referring now to FIGS. 10a–10c, there are shown transforms for an interior diameter pit, such as the pit 14 shown in FIG. 1. As is seen in FIG. 10c, the signal rotates clockwise initially as frequency increases from red to yellow and blue and then moves counter-clockwise at the highest frequencies of violet and magenta. Accordingly, it has similarities to the through-hole transforms of FIGS. 9a, 9b and 9c. However, the interior diameter pit transform increases in amplitude with increasing frequency. In addition, the composite phase angle α is substantially smaller than that of FIGS. 9a, 9b, and 9c.

Referring now to FIGS. 11a–11c, it is seen that the three lissajous figures represent a prior art display of detections of the through hole 12 (FIG. 11b), the magnetic inclusion 20 (FIG. 11a) and the roll stop 21, 22 (FIG. 11c), respectively. Neither the magnetic inclusion 20 nor the roll stop 21, 22 are anomalies which present a hazard, whereas as a deep interior diameter pit 14 or through hole 12 are anomalies which are hazardous and require replacement of the tube 10. The prior art eddy current signals of FIGS. 11a, 11b and 11c are substantially similar in appearance requiring a technician with considerable training and experience to distinguish the harmless anomalies from the hazardous anomaly. By utilizing the principles of the present invention, the nature of the detected anomaly is displayed with clarity.

In FIGS. 12a–12c, the color-coded transforms are from a detected anomaly in the form of a magnetic inclusion, such as the magnetic inclusion 20 of FIG. 1. As the frequency increases, there is a slight clockwise phase rotation of the transforms and increase in amplitude. The clockwise rotation is most readily apparent at the highest frequency, color-coded magenta, where the amplitude is greatest. Note the magenta tips 75 of the transforms of FIGS. 12a and 12b and the magenta tips 76 on the endpoint curves 77 of FIGS. 12c.

Figures 13A, 13B, 13C:
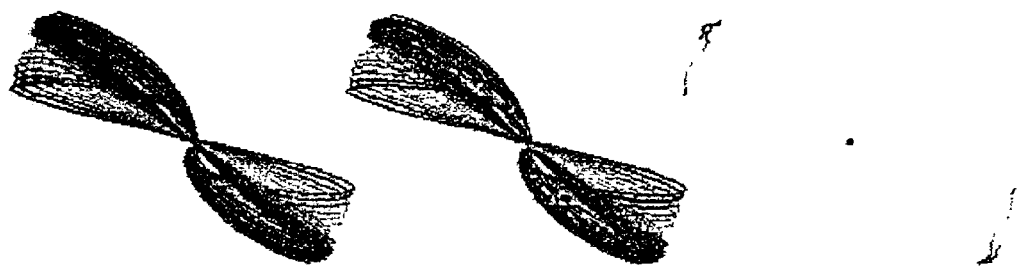
FIGS. 13a–13c are frequency transforms illustrating the detection of a through-wall hole.

Referring now to FIGS. 13a–13c, if the color-coded frequency transforms are from a through-wall hole, such as the through wall hole 12, then they resemble the transforms of FIGS. 9a, 9b and 9c which have a nearly constant amplitude as well as a change in phase rotation α from clockwise to counter-clockwise. The transforms for a deep internal pit such as the pit 14 are substantially different to the transforms for a through-hole 12, while the transform for any internal diameter pit has the signature of FIGS. 10a, 10b and 10c. Both the internal pit and through hole transforms differ substantially from the magnetic inclusion transform of FIGS. 12a–12c.

Figures 14A, 14B, 14C:
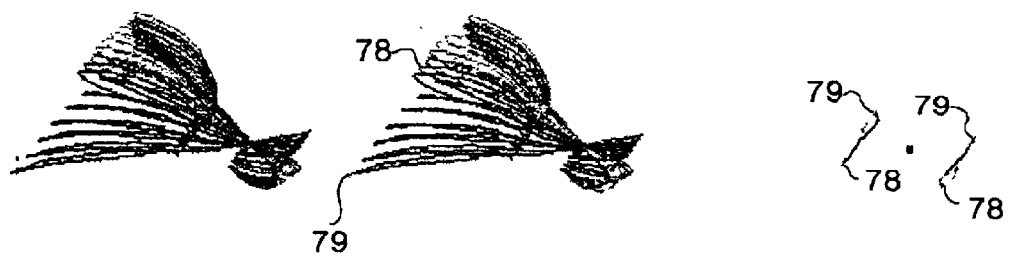
FIGS. 14a–14c are frequency transforms illustrating the detection of a roll stop.

Referring now to FIGS. 14a–14c, there are shown color-coded transforms from a detection of roll stop 21, 22. The roll stop 21,22 is actually a simultaneous thinning of the inside and the outside of the tube 10; therefore, an artificial roll stop can be machined into a standardized tube by machining a shallow outside diameter groove in the same axial position as a shallow inside groove. In these transforms, as frequencies increase from the low frequency 11 Khz red signal 78 to the high frequency 88 Khz magenta signal 79, it is seen that there is an increase in amplitude at the highest frequencies as well as a notable counter-clockwise phase angle rotation. It is clear that the transforms of FIGS. 14a–14c for a roll stop 22 are substantially different from the transforms of FIGS. 10a–10c for an internal diameter pit 14, the transforms of FIGS. 9a–9c and 13a–13c for a through hole 12 and the transforms of FIGS. 12a–12c for a magnetic inclusion 20.

Clearly, by writing lissajous figures for different frequency channels in different colors, and then superimposing those figures to create transforms, the distinctions are readily apparent between hazardous anomalies (such as interior diameter pits 14, exterior diameter pits 16, through-holes 12 and dents 18), and harmless anomalies (such as roll stops 22 and magnetic inclusions 20).

Figure 15A:
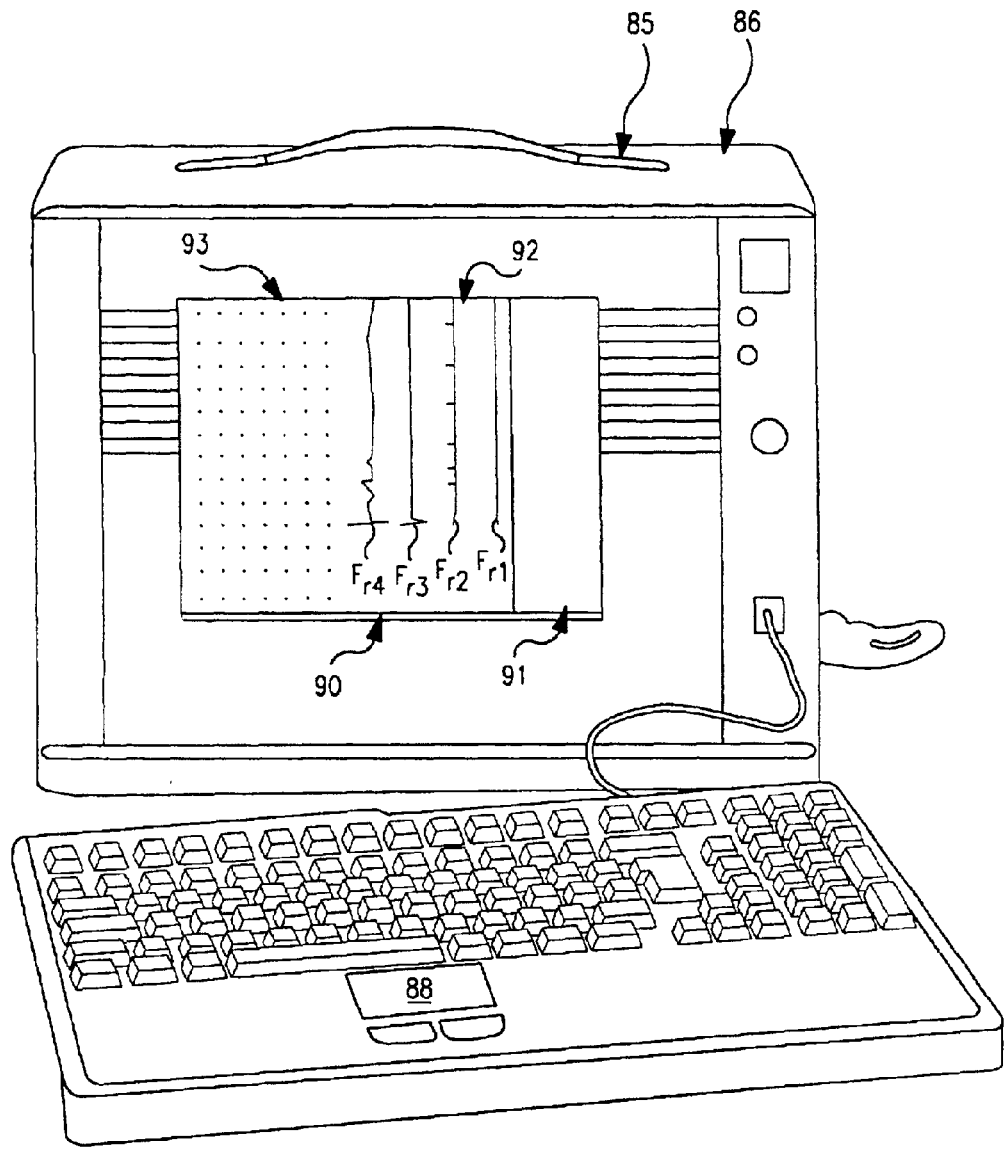

Referring now to FIG. 15a, in order to obtain the results illustrated in FIGS. 5–14, a computer controlled eddy current instrument 85 is used. Exemplary of such an instrument is the "ect™ MAD 8D, Multi-Frequency Eddy Current Instrument" available from Current Technology Incorporated which has been modified by reprogramming. The operation of this eddy current instrument is set forth in its accompanying manual, ect MAD 8D Manual, incorporated herein in its entirety by reference and filed as an appendix to this application.

Figure 15B:
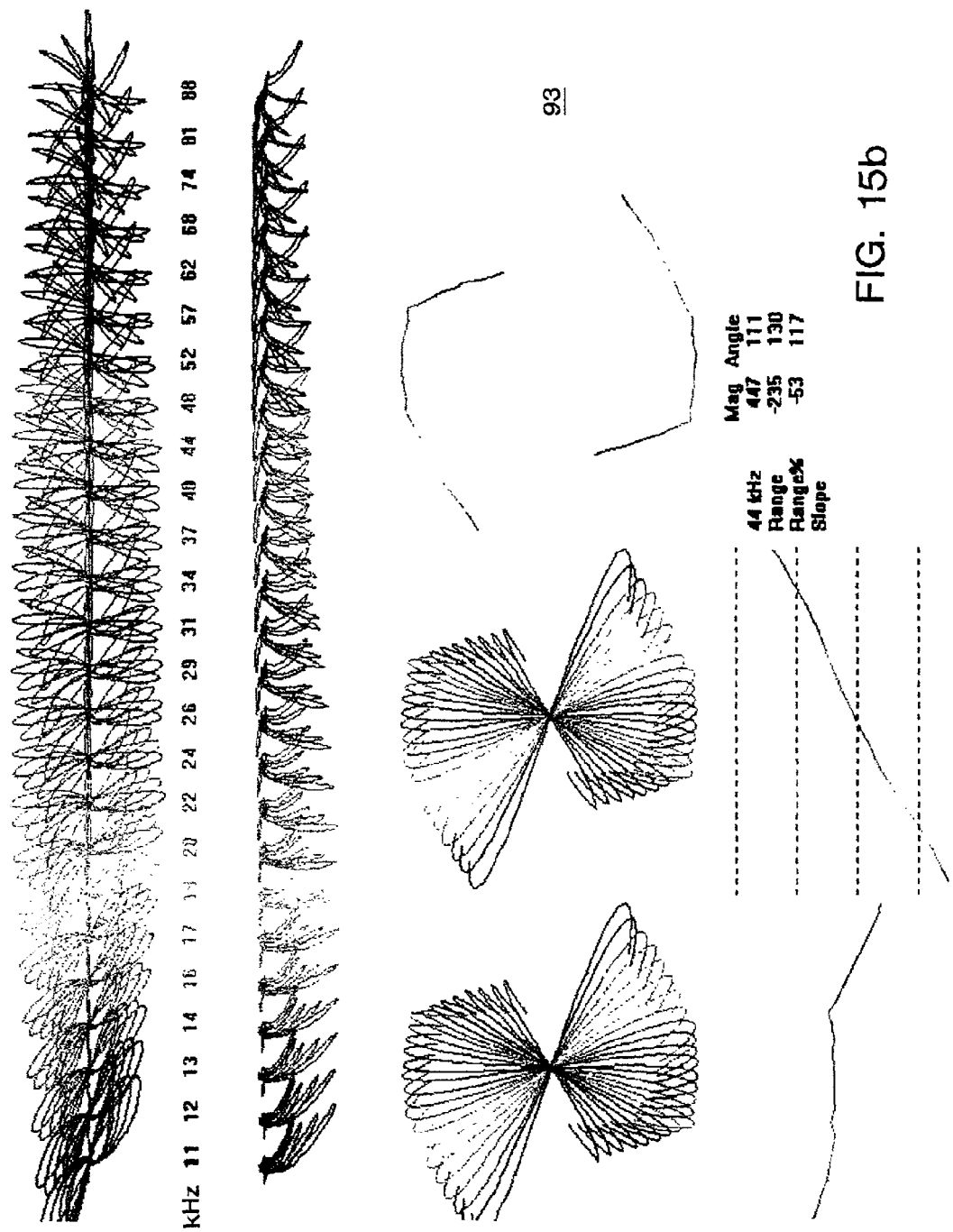

The eddy current test instrument 85 includes a probe such as the probe 25 of FIG. 1 which is connected to a computer 86. The computer 86 has been pre-programmed in accordance with known techniques to generate strip charts with frequency waveforms as well as lissajous figures such as those shown in FIGS. 2 and 4. Various colors are available from the computer 86 for displaying the strip charts, lissajous figures, and frequency channel transforms. The computer 86 is connected to a keypad 88 and to a screen 90. The screen 90 has its display area divided into a menu area 91, a strip chart area 92, and a lissajous figure transform area 93 which is shown in greater detail in FIG. 15b. The transform display area 93 displays the various transforms shown in FIGS. 5–14, while the strip chart displays horizontal and vertical components of the eddy current signal waveforms $Fr_1$–$Fr_4$. The waveforms Fr are four in number because it is the usual practice to apply four "real frequencies" to the excitation coil 30 of the probe 25 (see FIG. 1). The sinusoidal frequency waveforms $Fr_1$–$Fr_4$ are the frequency signals detected by receiving coils 30*a* and 30*b*, which are converted into the lissajous figures on display 93 (FIG. 15*b*) after having been processed in accordance with the principles of the present invention.

FIG. 17 illustrates steps for practicing the method of the present invention on apparatus within the computer 86, which apparatus is configured in accordance with the principles of the present invention. The computer 86 is initially programmed in accordance with the present invention by selecting four real frequencies $Fr_1$–$Fr_4$ which will be applied to the excitation coil 29 to produce eddy currents in the wall 11 of the tube 10 (see FIG. 1). While four frequencies $Fr_1$–$Fr_4$ are usually used for testing non-ferrous heat exchange tubes, it should be kept in mind that there may be more real frequencies Fr or fewer real frequencies Fr depending upon how the instrument 85 is being used. It is only important that the real excitation frequencies create the desired effect in the object under test. As selected from the frequency distinctions of FIG. 5 and for purposes of illustration, the real frequency $FR_1$ might be 11 Khz, the real frequency $FR_2$ might be 22 Khz, the real frequency $FR_3$ might be 44 Khz, and the real frequency $FR_4$ might be 88 Khz.

The principles of the present invention are used to generate virtual frequency signals FV between the real frequencies $FR_1$, $FR_2$, $FR_3$ and $FR_4$. In accordance with the frequency selections of FIGS. 5*a*–5*y* and 6*a*–6*y*, the transforms of the frequency channels of 12–20 Khz are virtual frequency channel transforms between the real frequency channels of 11 Khz and 22 Khz; the transforms of the frequency channel of 24–40 Khz are virtual frequency channels between the real frequency channels of 22 Khz and 44 Khz, while the transforms of the frequency channels 48–81 Khz are virtual frequency channels of between the real frequency channels of 44 Khz and 88 Khz. Consequently, there are twenty-five frequency channel transforms which are superimposed upon one another as shown in FIGS. 7*a*–7*c*. While twenty-five frequency channels have been selected for display, there may be more or fewer frequency channels made available for display.

Each of the virtual channels FV is generated from the real channels FR by interpolating the data from the real channels in order to obtain additional channels of data that represent the information that would be received if frequencies between the real frequencies used.

In the case of eddy current, the output from a single frequency channel is sampled, resulting in a horizontal and a vertical numeric value, which represents a point in a plane. Many samples are taken in time and these points are plotted in a plane. The resulting individual points are displeasing to the eye, so it is normal to fill in the points on the screen that fall between the sample points. This is done essentially by drawing a straight line between any two sample points in time which referred to as the straight line interpolation method. Another interpolation method, when there are multiple points available, is to draw the connecting line not straight but as a curve calculated by mathematic equations that calculate curves that provide a best fit to multiple points, such as a least squared error fit or by using polynomial equations. Virtual frequency channels FV are generated by connecting together the points of data from multiple frequency channels for the same or approximately the same sample in time, rather than connecting together two points from the same frequency channel, but at sequential times.

In the case of the lissajous FIGS. 5–14 where the figures are superimposed on each other from different frequency channels as in FIGS. 7–10 and 12–14, it is seen that by drawing a straight line between the end points of the lissajous figures, a straight line approximation of the end points of the virtual frequency channels is generated between the original real frequency channels FR. Considering these lissajous patterns as they were occurring in real time, it is seen that if for each sample in time a pont is calculated which is exactly between the two original points, a virtual frequency channel is generated. In the case of eddy current analysis, this is the data expected if you instead used the frequency that was a geometric mean (the square root of frequency one times frequency two) of the two real frequency channels.

Having generated the frequency channel which is midway between the original two real frequency channels, frequency channels are generated between each of the real channels FR and the first virtual channel. Any number of virtual channels FV can be generated. It is not necessary that one of these channels be exactly midway between two real channels. It would be, for example, possible to have two virtual channels which fall between to real channels. The first being one third of the distance from the first real channel to the second one, and the second virtual channel being approximately two thirds of the distance from the first real channel to the second real channel. The purpose of generating virtual frequency channels FV is to make frequency channel transforms more pleasing to the human eye and easier to understand.

A limited number of additional virtual channels can be generated by extrapolating the real frequency channels FR to obtain signals that represent frequency channels FR somewhat beyond the real frequency channels. For example, it may be useful to generate virtual frequency channels FV or perhaps 10 kHz and 94 kHz to bracket the channels of FIGS. 5*a*–5*y*.

There are many methods that can be used for calculating the virtual frequency channels FR. One method would be to take the vertical numeric value for real frequency channel one and real frequency channel two and take the average of these two values to get the vertical value for a virtual channel and the average of the two horizontal values to get the virtual horizontal value. The vertical average and horizontal average becomes the virtual frequency channel that is midway between the original two real frequency channels.

An alternate method averages analog voltages from original real (frequency) channels by simply connecting two residues in series between two vertical analog outputs and another two resistors in series between two horizontal analog outputs from the original frequency channels. The voltage that is derived at the junctions of these two pairs of resistors is the average of the original two vertical and two horizontal values. The new averaged vertical and horizontal analog signals are the new virtual channels.

Preferably, the computer 86 set up for eddy current inspections according to the present invention will have twenty-five frequency channels for the lissajous differential signals of FIGS. 5*a*–5*y* and twenty-five frequency channels set up for the lissajous absolute signals of FIGS. 6*a*–6*y*. Accordingly, there are fifty channels, each channel having a phase control and a gain control resulting in fifty phase controls and fifty gain controls. Programming the computer 85 to accommodate these features is accomplished by using the menu 91 on the screen 90.

The first task is to input the virtual frequencies FV by calling up a frequency menu 91 and inputting the real frequencies $FR_1$, $FR_2$, $FR_3$, and $FR_4$ in a table with the keyboard 88. The real frequencies $FR_1$, $FR_2$, $FR_3$, and $FR_4$ are then interpolated by an interpolator within the computer 95. The interpolator selects seven virtual frequencies FV between each of the four real frequencies to provide twenty-five frequency channels in a differential frequency channel table and twenty-five frequency channels in an absolute frequency channel table.

It is now necessary to adjust each frequency channel whether real or virtual to have the correct phase and gain settings. This can be accomplished by using the keypad 88 to select each of the twenty-five phase and gain controls from the menus 91 on the screen 90 and adjust each appropriately.

Using the computer 86 is necessary because even for an experienced eddy current operator, it is tedious and time consuming to adjust the phase controls for proper angle orientation on the screen 90 and the gain controls for proper signal sensitivity. This task would be virtually impossible for new technicians learning the technology. Frequency transforms such as those of FIGS. 5–14 require setting phase controls and gain controls very accurately.

Each of the 50 channels (25 for the differential transforms and 25 for the absolute transforms) must have an angle and amplitude reference. Two common references are provided by using dent signals (FIG. 8) for the phase angle reference $\alpha$ by adjusting the dent signal to be horizontal on the screen 90, and by using the through-hole signals (FIGS. 9 and 13) as the amplitude reference V by adjusting it to a specific amplitude, possibly one volt. Whether a dent signal is adjusted to be horizontal, vertical, or any other specified angle, or the through wall hole signal is adjusted to the amplitude of a defect signal to any specific value is unimportant, as long as a phase reference and a gain reference are adjusted to accurate values.

An alternate way to set angle and amplitude references is to use the through wall hole signal of FIGS. 9 and 13 as the angle $\alpha$ reference, adjusting it to about 40 or 45 degrees and to also use it for the amplitude reference to adjust it as indicated in the paragraph above. The angle and amplitude references that an operator may choose are essentially limitless because and frequency transforms are useful regardless of the angle and amplitude references chosen. Certainly the frequency transforms will have a different appearance if different angle and amplitude references are chosen, but each signal source, such as dent, through wall hole, magnetic inclusion, and roll stop, will have unique appearances given a chosen angle and amplitude reference.

The automatic computer adjustment is accomplished by having the operator pull a reference probe 25 through a calibration tube 10 to inform the computer 86 as the angle reference $\alpha$ and the magnitude reference V as well as to what levels these references should be adjusted to.

One method is to point with a cursor to a defect signal, such as the dent signal in the strip chart 92, and through selections in the menu 91 inform the computer 86 that this signal is the phase reference which is to be adjusted to zero. The operator then points to the through hole reference of FIG. 9 and through the menu 91 informs the computer 86 to adjust this amplitude to one volt. The computer 86 then makes these adjustment in all fifty channels. This is done by measuring the angle $\alpha$ of the dent signal of FIG. 5 as it is displayed on the screen and subtracting this angle from the current setting of the phase control in the eddy current system. Likewise, the current magnitude of the hole signal of FIG. 9 is measured and the ratio of target magnitude divided by actual magnitude is used as a multiplier to modify the existing gain control setting. For example, if the target amplitude is one volt and the current amplitude is "0.9", then the gain control is multiplied by "1/0.9", which will increase the gain control such that the next time that the defect is scanned, it will be "1".

This process works regardless of what defect, dent, or other signal is used as the phrase or the magnitude reference. Although the above described procedure is preferable, it would also be effective to use the hole signal as an angle reference (usually a value between 40 and 45 degrees in current practice) as well as for the amplitude reference. Other defect signals also could be used. For example, 360 degree symmetrical groove signals (FIG. 14) can be used as signal sources to set calibration. This approach has an advantage in that 360 degree signal sources, such as the groove signals of FIG. 14, provide signals that are more repeatable than defect signals such the hole signal of FIG. 10. This is because when the probe 25 passes the hole 14 (FIG. 1), it may be closer or farther from the probe. This results in a change in the signal, which is mostly a change in amplitude.

Rather than have an operator point to the defect signal which is the angle reference and to the defect signal which is the amplitude reference, it is possible to have these signal sources in a predetermined order in a standard calibration tube 10. For example, the dent 18 may be located closest to one end of the reference tube with the hole 12 being the next signal in the tube. In this manner, the operator scans the probe 25 through the reference tube 10 with the computer 86 knowing that the first signal encountered will be the dent signal of FIG. 8 and that the second signal will be the hole signal of FIG. 9. The computer 86 then uses dent detection to adjust the phase control correctly and uses the through wall hole detection to adjust the gain correctly. Other anomalies may be used for phase and gain references as mentioned in the above paragraph.

When defects are detected using the max rate method, the computer 86 looks at how rapidly the signal is moving in the impedance plane while differentiating the horizontal, the vertical, or horizontal squared plus vertical squared, to locate the fastest moving signal in time.

For the computer 86 to find the end points of an anomaly signal it identifies the center of the defect with the max rate method and then from that point in the data, looks in both directions to find the two points that are farthest from the center of the defect. It identifies these as being the end points. A slight modification of this technique is to use data points that are one or a few samples closer to the center than to the actual end point.

The computer 86 can measure a defect based on the end points which are the minimum and maximum vertical (or horizontal) values. However, this is an obsolete technique with respect to the present invention because this technique has been used only in compatibility with data analysis by the strip chart 92 before lissajous figures were in common use where defects are measured by the vertical to peak value.

In calibration table, the phase $\alpha$ and gain V of the real frequency intermittently toward the phase and gain of the next real frequency. In other words, the phase and gain from the second through the eighth frequency is advanced from the frequency toward the ninth frequency; the phase and gain of the tenth frequency through the sixteenth frequency is advanced from the ninth real frequency to the seventeenth frequency, and the phase and gain from the eighteenth through the twenty-fourth frequency is advanced from the seventeenth to real frequency to the twenty-fifth real frequency.

Thus far the invention has been presented in the specific embodiment of an eddy current testing arrangement. This invention, however, has other applications.

Referring to FIG. 16, there is shown a signal source 200 that produces multiple signals in an electronic form or a form that can be converted to electronic. For example is seismology the original signal is a sound wave which is converted to an electrical signal with a microphone or similar device. The signals are then digitized in an analog to digital converter 202 and adjusted in gain with a gain control 203 and rotated with a rotator 204. Rotation is generally necessary in the eddy current implementation; however, it may not be necessary in other implementations, such as seismic, sonar, and ekg. The multiple channels can then be converted into many more multiple channels, referred to as virtual channels, using an interpolation technique. If the signals have a DC component, the signals must then be brought to a standard baseline with a centering device. This is probably necessary in the eddy current implementation, although in the seismic implementation, generally these signals have no DC component and centering would not be required in this implementation. The signals are then displayed superimposed on a screen, such as a computer screen, using a different color for each of the channels, so that the channels are easily distinguished by colors. Other techniques for identifying the channels, such as using a different intensity of one color or black and white, or using any such other scheme that allows the individual channels to be identifiable on the screen may be employed.

The order of the components identified in FIG. 16 is not important. For example, in the seismic implementation, it is unlikely that the transducer used to detect vibration would have a DC component in its output, therefore, the centering device 206 is not necessary. In other cases, DC components can be eliminated with a simple RC low pass filter; specifically, a series capacitor followed by a resistor connected to ground.

The gain control 203 may be before or after the digital-to-analog converter 202. If before the analog-to-digital converter 202, then the gain control 203 is likely implemented by a potentiometer or by an analog multiplier (or multiplying digital-to-analog converter) with the signal going into one of the two multiplier inputs and a constant value into the other input, with the resulting gain adjust signal emerging from the output of the multiplier.

Likewise, the rotator 204 which is most probably necessary in the eddy current implementation, but may not be necessary in other implementations, may be before or after the digital-to-analog converter 202 and may be before or after the gain control 203. The rotator 204 may be implemented in an analog circuit prior to the gain control by using a dual sine/co-sine potentiometer or an analog multiplying circuit or a multiplying digital-to-analog converter. The degree of phase rotation is determined by the angle of the shaft in the potentiometer implementation or by values (usually sine and co-sine of the intended angle or change) in analog or digital form applied to the appropriate multiplier. The gain control 203 and rotator 204 may be combined into one set of multipliers or may be combined in one software routine.

The centering device 206 if implemented prior to the digital-to-analog converter, can be as simple as an RC circuit as stated above. If implemented after the analog to digital converter 202, the signal to be analyzed could be averaged by adding up the values for all the samples and the signal segment under consideration and dividing by the number of samples in order to crate an offset value that is subtracted from the original signal in order to remove a DC component. An alternate method would be to take a portion of the signal that is known to be the best value to center upon, and use that as the offset value to be subtracted from the original signal. In the aforedescribed eddy current implementation, this value was the average of the end points of the signal segment with the most rapid movement in the center of the defect signal.

Virtual channel generation can also be performed in analog form prior to the analog-to-digital converter 202 or at any other location in this data conversion scheme. This is an interpolation of adjacent channels. If implemented in the analog form prior to the analog-to-digital converter, it can simply be a resistor divider network as shown in FIG. 17, feeding into a high impedance amplifier. The resistors $r_1$ and $r_2$ are in value if it is desired to have the virtual channels fall in evenly spaced interpolations of the original two channels.

An advantage of creating the virtual channels in the analog form is its simplicity. The disadvantage is that then any of the functions, such as the analog-to-digital converter, gain, rotator, or centering, each have to be implemented for each virtual and real channel.

In the software implementation, a single virtual channel can be created from two original channels simply adding together the two values and dividing by two. Note that division by two is a single arithmetic shift right operation which is easily and quickly implemented in software. This new virtual channel can be referred to as the ½ channel.

To generate three virtual channels between two real channels, the center ½ channel is generated as indicated above, and the quarter channels can be generated by using as inputs to the identical software function one of the original channels and the half channel value, or being implemented by multiplying one channel by three and adding it to the value of the other channel and then dividing by four (which is a simple shift right two bit operation).

The virtual channel generation method indicated above results in straight line interpolation. As a result, in the eddy current implementation, the frequency transform displays as four straight lines rather than a curve. More complex methods can be used to provide for better interpolation.

The rotator 204 may not be necessary in all implementations, but is necessary in the aforedescribed eddy current implementation. In eddy current, the signal sources represent an impedance or voltage with real and imaginary components (or horizontal and vertical components or in phase and out of phase components.)

Referring now to FIGS. 18a and 18b, superimposed frequency channel signals 300 and 302 are shown for eddy current testing identifying a dent at 304 and through hole at 306 and 80%, 60%, 40% and 20% pits at 308, 310, 312 and 314, respectively. It is seen that for analog displays of sinusoidal frequency channel signals, superimposed color signals for different panels provide substantial information concerning the phenomenon studied.

The signals 300 and 302 resemble signals resulting from studying phenomenon such as for example the EKG and seismology signals. Thus, the techniques described in this application are useful in understanding signals studies in various fields.

From the foregoing description, one skilled in the art can easily ascertain the essential characteristics of this invention and, without departing from the spirit and scope thereof, can make various changes and modifications of the invention to adapt it to various usages and conditions.

Upon further study of the specification and appended claims, further objects and advantages of this invention will become apparent to those skilled in the art.

What is claimed is:

1. A method of displaying signals from real parameters obtained from monitoring a phenomenon, comprising:

while the phenomenon is being monitored producing multiple analog signals in electronic form, the multiple analog signals each having a standard characteristic and real parameters of different real values;

interpolating the analog signals to produce multiple virtual signals assigning a separate visual distinction to at least several of the multiple virtual signals to produce multiple visually distinct signals; and displaying the multiple visually distinct signals while superimposed with respect to one another.

2. The method of claim 1, further comprising digitalizing the analog signals and the virtual signals and then displaying the resulting digitalized signals in separate colors.

3. The method of claim 2, comprising adjusting the real values of the real parameters.

4. The method of claim 3, wherein the real parameters have real phase angle and real amplitude for each real signal.

5. The method of claim 4, wherein the phenomenon is a detected eddy current.

6. The method of claim 5, wherein the eddy current is an eddy current induced in a metallic object and wherein there is an anomaly in the form of a defect in the metallic object.

7. The method of claim 6, wherein the metallic object is a tube and the anomaly is a defect in the tube.

8. The method of claim 7, wherein the multiple real signals are produced with a differential probe, the method further including converting the multiple real and virtual signals to lissajous transforms generated by voltage vector sweeps and phase angles when the multiple signals are displayed.

9. The method of claim 8, wherein the anomaly is one occurring in a group of anomalies, comprising through holes, interior pits, exterior pits, magnetic inclusions, dents and roll stops, each of which has distinctive display of the multiple colored signals.

10. The method of claim 1, wherein the signals have different DC components, the method further comprising centering the signals by bringing the signals to a standard baseline.

11. The method of claim 1, comprising:

assigning a color to each signal to produce colored signals after interpolating the real signals to create the virtual signals, wherein the colored signals are in channels of increasing frequency and wherein the assigned colors are of increasing visible frequencies from a lowest visible frequency to a highest visible frequency.

12. The method of claim 11, wherein the display includes a waveform created by writing the lower visible frequency color first and superimposing a higher visible frequency color thereon in order from lower visible frequencies to higher visible frequencies.

13. The method of claim 12, wherein the display includes a waveform created by writing higher visible frequency colors in an order from higher visible frequencies to lower visible frequencies with a color being assigned to the highest frequency signal which contrasts with the highest visible frequency.

14. The method of claim 13, wherein the display includes a plot of only the end points of the waveforms.

15. The method of claim 13 wherein the waveforms of the display are continuous curves.

16. The method of claim 12, wherein the display includes a plot of only the end points of the waveforms.

17. The method of claim 12 wherein the waveforms of the display are continuous curves.

* * * * *

UNITED STATES PATENT AND TRADEMARK OFFICE
CERTIFICATE OF CORRECTION

PATENT NO.          : 7,095,410 B2                                           Page 1 of 1
APPLICATION NO.  : 09/740042
DATED                  : August 22, 2006
INVENTOR(S)         : Monty O'connor It is certified that error appears in the above-identified patent and that said Letters Patent is hereby corrected as shown below:

On the front page, Title: line 1, reads "METHOD" should read -- METHODS --
Column 16, line 15, reads "real signals" should read -- analog signals --

Signed and Sealed this

Thirteenth Day of February, 2007

JON W. DUDAS
*Director of the United States Patent and Trademark Office*